US007135584B2

(12) United States Patent
Kucera et al.

(10) Patent No.: US 7,135,584 B2
(45) Date of Patent: *Nov. 14, 2006

(54) LIPID ANALOGS FOR TREATING VIRAL INFECTIONS

(75) Inventors: Louis S. Kucera, Pfafftown, NC (US); Susan L. Morris-Natschke, Apex, NC (US); Khalid S. Ishaq, Chapel Hill, NC (US)

(73) Assignees: Wake Forest University, Winston Salem, NC (US); University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/889,127

(22) Filed: Jul. 13, 2004

(65) Prior Publication Data

US 2004/0259845 A1     Dec. 23, 2004

Related U.S. Application Data

(60) Continuation of application No. 09/412,539, filed on Oct. 4, 1999, which is a division of application No. 08/793,470, filed as application No. PCT/US95/10111 on Aug. 7, 1995, now Pat. No. 5,962,437.

(51) Int. Cl.
C07F 9/02 (2006.01)
A61K 31/685 (2006.01)
A61P 31/12 (2006.01)

(52) U.S. Cl. ............ 558/166; 558/169; 558/170; 558/172; 558/174; 514/77

(58) Field of Classification Search ............ 514/77; 558/166, 169, 170, 172, 174
See application file for complete search history.

(56) References Cited

U.S. PATENT DOCUMENTS

| 2,086,585 A | 7/1937 | Taub et al. ............ 260/127 |
| 2,087,132 A | 7/1937 | Taub et al. ............ 260/127 |
| 2,108,765 A | 2/1938 | Domagk ............ 167/30 |
| 2,209,383 A | 7/1940 | Bock ............ 8/116 |
| 2,439,969 A | 4/1948 | Fourneau ............ 260/338 |
| 2,445,393 A | 7/1948 | Fourneau ............ 260/338 |
| 2,513,747 A | 7/1950 | Sallman et al. ............ 260/338 |
| 2,606,909 A | 8/1952 | Blicke ............ 260/338 |
| 2,689,790 A | 9/1954 | Mowry et al. ............ 71/2.7 |
| 2,950,253 A | 8/1960 | Kling et al. ............ 252/152 |
| 3,054,678 A | 9/1962 | Michener et al. ............ 99/150 |
| 3,694,473 A | 9/1972 | Eibl et al. ............ 260/403 |
| 4,093,714 A | 6/1978 | Tolman et al. ............ 424/180 |
| 4,096,278 A | 6/1978 | Queuille ............ 424/329 |
| 4,119,714 A | 10/1978 | Kny et al. ............ 424/199 |
| 4,159,988 A | 7/1979 | Eibl et al. ............ 260/340.9 R |
| 4,221,732 A | 9/1980 | Oette et al. ............ 260/403 |
| 4,235,877 A | 11/1980 | Fullerton ............ 424/89 |
| 4,291,024 A | 9/1981 | Turcotte ............ 424/180 |
| 4,329,302 A | 5/1982 | Hanahan et al. ............ 260/925 |
| 4,426,525 A | 1/1984 | Hozumi et al. ............ 546/22 |
| 4,444,766 A | 4/1984 | Bosies et al. ............ 424/211 |
| 4,471,113 A | 9/1984 | MacCoss ............ 536/20 |
| 4,540,521 A | 9/1985 | Garst et al. ............ 260/459 A |
| 4,559,157 A | 12/1985 | Smith et al. ............ 252/90 |
| 4,608,392 A | 8/1986 | Jacquet et al. ............ 514/844 |
| 4,619,917 A | 10/1986 | Lee et al. ............ 514/77 |
| 4,622,392 A | 11/1986 | Hong et al. ............ 536/29 |
| 4,661,509 A | 4/1987 | Gordon et al. ............ 514/397 |
| 4,724,232 A | 2/1988 | Rideout et al. ............ 514/50 |
| 4,797,479 A | 1/1989 | Shuto et al. ............ 536/27 |
| 4,816,450 A | 3/1989 | Bell et al. ............ 514/25 |
| 4,820,508 A | 4/1989 | Wortzman ............ 424/59 |
| 4,826,823 A | 5/1989 | Cook et al. ............ 514/46 |
| 4,835,263 A | 5/1989 | Nguyen et al. ............ 536/27 |
| 4,837,023 A | 6/1989 | Eibl ............ 424/439 |
| 4,841,039 A | 6/1989 | Chu et al. ............ 536/29 |
| 4,880,782 A | 11/1989 | Eckstein et al. ............ 514/45 |
| 4,921,951 A | 5/1990 | Shuto et al. ............ 536/27 |
| 4,938,949 A | 7/1990 | Borch et al. ............ 424/10 |
| 4,992,478 A | 2/1991 | Geria ............ 514/782 |
| 4,997,761 A | 3/1991 | Jett-Tilton ............ 435/240.2 |
| 5,026,687 A | 6/1991 | Yarchoan et al. ............ 514/45 |
| 5,034,394 A | 7/1991 | Daluge ............ 514/261 |
| 5,138,045 A | 8/1992 | Cook et al. ............ 536/27 |
| 5,221,696 A | 6/1993 | Ke et al. ............ 514/786 |

FOREIGN PATENT DOCUMENTS

| DE | 37 26 945 A1 | 2/1989 |
| DE | 39 34 820 A1 | 4/1991 |
| DE | 40 10 228 A1 | 10/1991 |
| EP | 0 094 586 | 11/1983 |
| EP | 0 109 255 | 5/1984 |
| EP | 0 142 333 | 5/1985 |
| EP | 0 145 303 | 6/1985 |

(Continued)

OTHER PUBLICATIONS

Aggarwal, S. K. et al., "Synthesis and Biological Evaluation of Prodrugs of Zidovudine," *J. Med. Chem.*, 33, 1505-10, 1990.

(Continued)

*Primary Examiner*—Brenda Coleman
(74) *Attorney, Agent, or Firm*—Morgan Lewis & Bockius LLP

(57) ABSTRACT

A method of treating viral infections, and in particular HIV-1, hepatitis B virus, and herpes virus, is disclosed. The method comprises administering to a subject in need of such treatment an infection-controlling amount of a phospholipid or phospholipid derivative.

18 Claims, No Drawings

FOREIGN PATENT DOCUMENTS

| | | |
|---|---|---|
| EP | 0 146 258 | 6/1985 |
| EP | 0 252 310 | 1/1988 |
| EP | 0 310 109 | 4/1989 |
| EP | 0 335 396 | 4/1989 |
| EP | 0 348 859 | 1/1990 |
| EP | 0 350 287 | 1/1990 |
| EP | 0 416 401 | 3/1991 |
| EP | 0 434 450 | 6/1991 |
| EP | 0 506 704 | 7/1991 |
| FR | 1561630 | 3/1969 |
| GB | 2 239 243 A | 6/1991 |
| JP | 42-13841 | 8/1967 |
| JP | 49-100224 | 9/1974 |
| JP | 61-238793 | 10/1986 |
| JP | 10-293129 | 11/1989 |
| WO | 90/00555 | 1/1990 |
| WO | 90/05736 | 5/1990 |
| WO | 90/15601 | 12/1990 |
| WO | 91/05558 | 5/1991 |
| WO | 91/09602 | 7/1991 |
| WO | 91/18914 | 12/1991 |
| WO | 91/19726 | 12/1991 |
| WO | 92/03462 | 3/1992 |
| WO | 92/06192 | 4/1992 |
| WO | 93/00910 | 1/1993 |
| WO | 93/08807 | 5/1993 |
| WO | 93/16091 | 8/1993 |
| WO | 93/16092 | 8/1993 |
| WO | 93/17020 | 9/1993 |
| WO | 93/21191 | 10/1993 |

OTHER PUBLICATIONS

Amari, J. V. et al., "Isolation of Experimental Anti-AIDS Glycerophospholipids by Micro-Preparative Reversed-Phase High-Performance Liquid Chromatography," *Journal of Chromatography*, 590, 153-161, 1992.

Anderson, L. J. et al., "Antigenic Characterization of Respiratory Syncytial Virus Strains with Monoclonal Antibodies," *Journal of Infectious Diseases*, 151:626-633, Apr. 1985.

Berdel, W. E. et al., "Cytotoxicity of Thioether-Lysophospholipids in Leukemias and Tumors of Human Origin," *Cancer Research*, vol. 43, 5538-5543, 1983.

Boldanova, N. B. et al., "Protective Effect of Phosphatidylcholine-Containing Liposomes in Experimental Toxic Hepatitis," *Vopr. Med. Khim*, 32, No. 3 (1986) Chemical Abstracts 105, p. 67, Abstract No. 35587k (1986).

Bosies, E. et al., "Preparation of Lecithin Analogs as Retrovirucides and Virucides," *Chemical Abstracts*, 115CA; 72142p, 1991.

Caliendo, A. M. et al., "Combination Therapy for Infection Due to Human Immunodeficiency Virus Type 1", *Clinical Infectious Diseases*, vol. 18, pp. 516-524, 1994.

Chen, X. et al., "Design and Synthesis of Novel Nucleoside Analogs as Potential Antiviral Agents," Abstract *American Assoc. of Pharmaceutical Scientists*, vol. 9, No. 10, 1992.

Coe, D. M. et al., "Preparation of Nucleotide Mimics with Potent Inhibitory Activity Against HIV Reverse Transcriptase," *J. Chem. Soc. Perkin Trans 1*, 3378-3379, 1991.

Crumpton, S. et al., "Novel Lipid Analogs with Cytostatic and Cytocidal Activity," *Anticancer Research*, vol. 8, No. 6, pp. 1361-1366, Nov.-Dec. 1988.

Daniel, L. W. et al., "Alkyl-Linked Diglygerides Inhibit Protein Kinase C Activation by Diacylglycerols," *Biochemical & Biophysical Research Communications*, 151, 291-97, Feb. 29, 1988.

Daniel, L. W. et al., "Characterization of Cells Sensitive and Resistant to ET-18-OCH$_3$," Abstract 2447, *Proceedings of the American Assoc. for Cancer Res.*, 31, 416, Mar. 1990.

Dietzfelbinger, "Cytotoxic and Purging Effects of ET-18-OCH3 in Human Malignant Lymphoid Cell Lines in Vitro," Abstract 2472, *Proceedings of the American Assoc. for Cancer Res.*, 31, 416, Mar. 1990.

Falsey A. R. et al., "Viral Respiratory Infections in the Institutionalized Elderly: Clinical and Epidemiologic Findings," *J Am Geriatric Soc.*, 40:115-119, 1992.

Fields, A. P. et al., "Human Immunodeficiency Virus Induces Phosphorylation of its Cell Surface Receptor," *Nature*, 333, 278-80, May 19, 1988.

Fujiwara K., et al., "Comparison of Cell Kill Induced by Two Ether Lipids in Combination with Hyperthermia," *Proceedings of the American Association for Cancer Research; Preclinical Pharmacology Experimental Therapeutics*, vol. 31, pp. 416, Abstract 2467, Mar. 1990.

Gill, P. S. et al., "Azidothymidine Associated with Bone Marrow Failure in the Acquired Immunodeficiency Syndrome (AIDS)", *Annals of Internal Medicine* 107: 502-505, 1987.

Glezen, W. P. et al., "Risk of Primary Infection and Reinfection with Respiratory Syncytial Virus," *Am J Dis Child*, 140:543-546, 1986.

Gordeev, K. et al., "Synthesis of Thio Analogs of Platlet Activating Factor (PAF)," *Bioorg. Khim.*, vol. 12, No. 7, pp. 951-955, 1986.

Graham, F. L. et al., "A New Technique for The Assay of Infectivity of Human Adenovirus 5-DNA," *Virology*, vol. 52, pp. 456-467, 1973.

Hall, C. B. et al., "Infectivity of Respiratory Syncytial Virus by Various Routes of Inoculation," *Infect Immun.*, 33:779-783, 1981.

Hall, C. B. et al., "Nosocomial Respiratory Syncytial Virus Infections," *N Engl J Med*, 293:1343-1346, 1975.

Hall, C. B. et al., "Respiratory Syncytial Virus Infections Within Families," *N Engl J Med*, 294:414-419, 1976.

Hancock, J. et al., "Analogs of Natural Lipids. VII. Synthesis of Cyclopentanoid Analogs of Phosphatidylcholine," *Journal of Lipid Research*, vol. 23, 183-189, 1982.

Harada, S. et al., "Infection of HTLV-III/LAV in HTLV-I-Carrying Cells MT-2 and MT-4 and Application in a Plaque Assay," *Science*, 229, 563-566, Aug. 9, 1985.

Hayashi, M et al., "Antitumor Activity of a Novel Nucleotide Derivative, 5'-(1,2 Dipalmitoyl-*sn*-glycero-3-phospho)-5-fluorouridine (TJ14026) on Murine Tumors," *Biol. Pharm. Bull.*, 16(8), 778-81, 1993.

Henderson, F. W. et al., "Respiratory-Syncytial-Virus Infections, Reinfections, and Immunity: a Prospective, Longitudinal Study in Young Children," *N Engl J Med,*, 300:530-534, 1979.

Hendrickson, H. S. et al., "A Facile Asymmetric Synthesis of Glycerol Phospholipids via Tritylglycidol Prepared by the Asymmetric Epoxidation of Allyl Alcohol, Thiolester and Thioether Analogs of Phosphatidylcholine", *Chemistry and Physics Lipids*, vol. 53, No. 1, pp. 115-120, 1990.

Himmelmann, A. W. et al., "Studies on the Cross Resistance Pattern of Membrane-Toxic Lipids in Vitro," *Abstract 2448, Proceedings of the American Assoc. for Cancer Res.*, 31, 416, Mar. 1990.

Hong, C. I. et al., "Nucleoside Conjugates. 15. Synthesis and Antitumor Activity of 1-β-D-Arabinofuranosylcytosine and Cytidine Conjugates of Thioether Lipids", *Journal of Medicinal Chemistry* 33: 1380-1386, 1990.

Hong, C. et al., "Formulation, Stability and Antitumor Activity of 1-β-D-Arabinofuranosylcytosine Conjugate of Thioether Phospholipid", *Cancer Res.* 50: 4401-4406, 1990.

Hong, C. et al., "Nucleoside-Ether Lipid Conjugates as Biotransformed Prodrugs of Antitumor and Antiviral Nucleosides," Abstract *J. Lipid Mediators Cell Signaling*, vol. 10. No. 1-2, pp. 159-161, 1994.

Hostetler, K. et al., "Antiviral Activity of Phosphatidyl-Dideoxycytidine in Hepatitis B-infected Cells and Enhanced Hepatic Uptake in Mice," *Antiviral Research,*, 59-67, 1994.

Hostetler, K. et al., "Synthesis and Antiretroviral Activity of Phospholipid Analogs of Azidothymidine and Other Antiviral Nucleosides," *Journal of Biological Chemistry*, 265: 6112-6117, 1990.

Hostetler et al., "Phosphatidylazidothymidine: Mechanism of Antiretroviral Action in CEM Cells," *Journal of Biological Chemistry*, 266: 11714-11717, 1991.

Hruska, J. F. et al., "In Vivo Inhibition of Respiratory Syncytial Virus by Ribavirin," *Antimicrob Agents Chemother.*, 21:125-130, 1982.

Hsu, L. et al., "Synthesis of Anti-Restricted Pyrimidine Acyclic Nucleosides," *Journal of Organic Chemistry*, vol. 57, No. 12, pp. 3354-3358, 1992.

Jahne, G. et al., "Preparation of Carbocyclic Phosphonate Nucelosides," *Tetrahedron Letters*, vol. 33, No. 37, 5335-5338, 1992.

Jayasuriya, N. et al., "Design, Synthesis, and Activity of Membrane-Disrupting Bolaphiles," *J. Am. Chem. Soc.*, 112, 5844-5850, 1990.

Jia, C. et al., "Diamide Analogues of Phosphatidyl Choline as Potential Anti-AIDS Agents," *J. Chem. Soc.*, 2521-2523, 1993.

Kakiuchi, N. et al., "Non-peptide Inhibitors of HCV Serine Proteinase," *J. FEBS Letters*, 421:217-220, 1998.

Kasnar, B. et al., "Synthesis of 2',3'-Dideoxy- and 3'-Azido-2',3'Dideoxy-Pyridazine Nucleosides as Potential Antiviral Agents," *Nucleosides & Nucleotides*, 13(1-3), pp. 459-479, 1994.

Kawana, F. et al., "Inhibitory Effects of Antiviral Compounds on Respiratory Syncytial Virus Replication In Vitro," *Antimicrob Agents Chemother*, (8):1225-30, Aug. 31, 1987.

Korba, B. E. et al., "Use of a Standardized Cell Culture Assay to Assess Activities of Nucleoside Analogs Against Hepatitis B Virus Replication," *Antiviral Research*, 19, 55-70, 1992.

Krugner-Higby, L. A. et al., "Novel Membrane Interactive Ether Lipid Analogs Inhibit HIV-1 Glycoprotein Interaction with $CD4^+$ Cells," Abstract 321, $32^{nd}$ *Interscience Conf. on Antimicrobial Agents and Chemotherappy*, Anaheim, 164, Oct. 11-14, 1992.

Kucera, L. S., et al., "Activity of Triciribine and Triciribine-5'-Monophosphate Against Human Immunodeficiency Virus Types 1 and 2k" *Aids Research and Human Retroviruses*, vol. 9, No. 4, pp. 307-314, 1993.

Kucera, L. S. et al., "Effect of Membrane-Active Ether Lipid (EL) Analogues on Human Immunodeficiency Virus Production Measured by Plaque Assay," *Annuals of the New York Academy of Sciences*, vol. 616, 545-548, Dec. 26, 1990.

Kucera, L. S. et al., "Inhibition of HIV-1 Plaque Formation by a Novel Class of Membrane-Active Ether Lipid Analogs," *International Conference on AIDS*, Abstract No. W.C.O. 21, p. 528, Jun. 4-9, 1989.

Kucera, L. et al., "Inhibition of Human Immunodeficiency Virus-1 (HIV-1) by Novel Membrane Interactive Ether Lipids," Abstract No. 2470, *Proceedings of the American Assoc. for Cancer Res.*, 31, 416, May 23-26, 1990.

Kucera, L., et al., "Inhibition of Human Immunodeficiency Virus Envelope Glycoprotein-Mediated Cell Fusion by Synthetic Phospholipid Analogs," *Antiviral Research*, p. A260, 1985.

Kucera, L. S. et al., "Investigations on Membrane Active Ether Lipid Analogs that Alter Functional Expression of HIV-1 Induces Glycoproteins and Inhibit Pathogenesis," Abstract, *Journal of Cellular Biochemistry*, 17E Suppl:16, 1993.

Kucera, L., et al., "Novel Ether Lipid Analogs of Platelet Activating Factor with Anti-Hepatitis B Virus Activity," Abstract H125, *ICAAC Orlando*, Oct. 4-7, 1994.

Kucera, L. et al., "Novel Membrane-Interactive Ether Lipid Analogs That Inhibit Infectious HIV-1 Production and Induce Defective Virus Formation," *AIDS Research And Human Retroviruses*, 6, 491-501, 1990.

Kucera, L. S. et al., "Novel Membrane Interactive Ether Lipids with Anti-Human Immunodeficiency Virus Activity", *Membrane Interactions of HIV*, pp. 329-350, 1992.

Kumar, R., et al., "Equal Inhibition of HIV Replication by Steroisomers of Phosphatidyl-Azidothymidine—Lack of Stereospecificity of Lysosomal Phospholipase $A_1$," *The Journal of Biological Chemistry*, 267, 20288-20292, 1992.

Larder, B. A. et al., "HIV with Reduced Sensitivity to Zidovudine (AZT) Isolated During Prolonged Therapy", *Science* 243: 1731-1734, 1989.

Lister, M. D. et al., "Cyclopentanoid Analogs of Phosphatidylcholine: Susceptibility to Phospholipase $A_2$," *Journal of Lipid Research*, vol. 29, 1297-1308, 1988.

MacCoss, M. et al., "Synthesis and Biological Activity of Novel Nucleoside-Phospholipid Prodrugs," *4th International Round Table Nucleosides, Nucleotides and their Biological Applications*, Antwerp, p. 255-263, Feb. 4-6, 1981.

Marasco, Jr., C. J., "The Synthesis and Biological Activity of Novel Alkylglycerol Derivatives as Inhibitors of Protein Kinase C Activity, Neoplastic Cell Growth, and HIV-1 Infectivity," *Dissertation for Ph.D., Univ. of No. Carolina, Chapel Hill*, 1990.

Marasco, C. J. et al., "Synthesis and Biological Activity of Novel Quaternary Ammonium Derivatives of Alkylglycerols as Potent Inhibitors of Protein Kincase C," *Journal of Medicinal Chemistry*, No. 33, pp. 985-992, Mar. 1990.

Marasco, C. J. et al., "The Synthesis and Biological Testing of Alkyl Glycerols as Potential Inhibitors of Protein Kinase C," *American Assoc. of Pharmaceutical Scientists Abstract*, vol. 5, No. 10, Oct. 1988.

Marx, M. H. et al., "Synthesis and Evaluation of Neoplastic Cell Growth Inhibition of 1-*N*-Alkylamide Analogues of Glycero-3-Phosphocholine," *Journal of Medicinal Chemistry*, 31, 858-863, Apr. 1988.

Meert, K. L. et al., "Aerosolized Ribavirin in Mechanically Ventilated Children with Respiratory Syncytial Virus Lower Respiratory Tract Disease: a Prospective Double-Blind Randomized Trial," *Crit Care Med.*, Abstract 22:566-572, Apr. 1994.

Mertes, M. P.et al., "Charge-Spatial Models. *cis*- and *trans*-3- and -4- Substituted Cyclohexyl Phosphates as Analogs of 2'-Deoxyuridine 5'-Phosphate," *Journal of Medicinal Chemistry*, vol. 12(5), 828-832, Sep. 1969.

Meyer, K. L., et al., "In Vitro Evaluation of Phosphocholine and Quaternary ammonium Containing Lipids as Novel Anti-HIV Agents," *Journal of Medicinal Chemistry*, 34, 1377-1383, 1991.

Meyer, K. L. et al., "Synthesis and Evaluation of Anti-HIV-1 Ether Lipids," *American Association of Pharmaceutical Scientists Abstract N. MN-510*, p. S-41, Sep. 1989.

Miller, R. H., et al., "Common Evolutionary Origin of Hepatitis B Virus and Retroviruses," *Proc. Natl. Acad. Sci. USA*, 83, pp. 2531-2535, Apr. 1986.

Mitsuya, H. et al., "Strategies for Antiviral Therapy in AIDS," *Nature*, 325, 773-78, Feb. 26, 1987.

Modest, "Combination Chemotherapy Studies with Antitumor and Antiviral Ether Lipid Analogs," Abstract 2471, *Proceedings of the American Assoc. for Cancer Res.*, 31, 416 Abstract 2471, Mar. 1990.

Modest, E. J. et al., "Pharmacological Effects and Anticancer Activity of New Ether Phospholipid Analogs," *The Pharmacological Effect of Lipids III: Role of Lipids in Cancer Research*, (In Press), pp. 330-337, 1989.

Morrey, J. D. et al., "Effects of Zidovudine on Friend Virus Complex Infection in Rfv-$3^{r/s}$ Genotype-Containing Mice Used as a Model for HIV Infection," *Journal of Acquired Immune Deficiency Syndromes*, 3, 500-10, 1990.

Morris-Natschke, S. L. et al., "Synthesis of Phosphocholine and Quaternary Amine Ether Lipids and Evaluation of *in Vitro* Antineoplastic Activity," *J. Med. Chem.*, 36:2018-2025, 1993.

Morris-Natschke, S. et al. "Synthesis of Sulfur Analogues of Alkyl Lysophosphopholipid and Neoplastic Cell Growth Inhibitory Properties," *J. of Med. Chem.*, 29, 2114-17, 1986.

Mutson, M. A. et al., "Two Distinct Subtypes of Human Respiratory Syncytial Virus," *The Journal of General Virology*, 66:2111-2124, Oct. 1985.

Nara, P. L. et al., "Simple, Rapid, Quantitative, Syncytium-Forming Microassay for the Detection of Human Immunodeficiency Virus Neutralizing Antibody," *AIDS Research and Human Retroviruses*, 3, 283-302, 1987.

Noseda, A. et al., "*In Vitro* Antiproliferative Activity of Combinations of Ether Lipid Analogues and DNA-interactive Agents Against Human Tumor Cells," *Cancer Research*, 48, 1788-1791, Apr. 1, 1988.

Noseda, A. et al., "Neoplastic Cell Inhibition with New Ether Lipids Analogs," *Lipids*, 22, 878-883, Nov. 1987.

Ostertag, W. et al., "Induction of Endogenous Virus and of Thymidine Kinase by Bromodeoxyuridine in Cell Cultures Transformed by Friend Virus," *Proc. Nat. Acad. Sci. USA*, 71, 4980-85, Dec. 1974.

Pacheco, D. Y. et al., "Mechanisms of Toxicity of Hepsulfam in Human Tumor Cell Lines," Abstract 2446, *Proceedings of the American Association for Cancer Research*, 81, 412, May 1990.

Painuly, P. et al., "Preparative HPLC of an Experimental Anti-HIV Analogue of AZT: Azidothymidine Monophosphate Diglyceride (AZT-MP-DG)," *Journal of Liquid Chromatography*, 16(11), 2237-2248, 1993.

Pajouhesh, H. et al., "Synthesis of Polar Head Group Homologs of All-trans-cyclopentano-phosphatidylcholine, Phosphatidyl-N, N-Dimethylethanolamine, and Phosphatidylethanolamine," *Journal of Lipid Research*, vol. 25, 294-303, 1984.

Piantadosi, C. et al., "Synthesis and Evaluation of Novel Ether Lipid Nucleoside Conjugates for Anti-HIV-1 Activity," *J. Med. Chem.*, 34, 1408-14, 1991.

Pidgeon, C. et al., "Antiviral Phospholips Anti-HIV Drugs Conjugated to the Glycerobackbonc of Phospholipids," *The Journal of Biological Chemistry*, 7773-7778, 1993.

Pidgeon C. et al., "Novel Acylated Phospholipid Drugs for AIDS," *Chemical Abstract*, 120:69591, 1994.

Poiesz, B. J. et al., "Detection and Isolation of Type C Retrovirus Particles From Fresh and Cultured Lymphocytes of a Patient with Cutaneous T-Cell Lymphoma", *Proc. Natl Acad. Sci. U.S.A.* 77: 7415-7419, 1980.

The PREVENT Study Group, "Reduction of Respiratory Syncytial Virus Hospitalization Among Premature Infants and Infants with Bronchopulmonary Dysplasia Using Respiratory Syncytial Virus Immune Globulin Prophylaxis," *Pediatrics*, 99:93-99, 1997.

Prince, G. A., "The Pathogenesis of Respiratory Syncytial Virus Infection in Cotton Rats," *Am J Pathol Abstract.*, 93:771-91, 1978.

Qiu, X. et al., "Membrane Properties of Antiviral Phospholipids Containing Heteroatoms in the Acyl Chains," *Biochemistry*, 33(4), 960-72, 1994.

Raetz, C. R. H. et al., "A Phospholipid Derivative of Cytosine Arabinoside and its Conversion to Phosphatidylinositol by Animal Tissue," *Science* 196, 303-304, 1977.

Richman, D. D. et al., "The Toxicity of Azidothymidine (AZT) in the Treatment of Patients with AIDS and AIDS-Related Complex", *New England Journal of Medicine* 317: 192-197, 1987.

Runge, M. H. et al., "Destruction of Human Solid Tumors by Alkyl Lysophospholipids," *Journal of the National Cancer Institute*, vol. 64, 1301-1306, 1980.

Sarin, P. S. et al., "Effects of a Novel Compound (AL 721) on HTLV-III Infectivity in Vitro," *The New England Journal of Medicine*, vol. 313, 1289-90, Nov. 14, 1985.

Scolaro M. J. et al., "Inhibition of Virus Replication with Oligonucleotides," Chemical Abstracts, 117:124476, 1992.

Sidoti, C. et al., "Cytostatic Activity of New Synthetic Anti-Tumor AZA-Alkyllysophospholipids," *Int. J. Cancer* 51, 712-717, 1992.

Smith, D. W. et al., "A Controlled Trial of Aerosolized Ribavirin in Infants Receiving Mechanical Ventilation for Severe Respiratory Syncytial Virus Infection," *New England Journal of Medicine*, 325:24-29, Jul. 1991.

Steim, J. M. et al., "Lipid Conjugates of Antiretroviral Agents. I. Azidothymidine-Monophosphate-Digylceride: Anti-HIV Activity, Physical Properties, and Interaction with Plasma Proteins," *Biochemical and Biophysical Research Communications*, vol. 171, No. 1, 451-457, 1990.

Sunamoto, J. et al., "Induction of Cytotoxic T Cell," *Chemical Abstracts*, 117:68365, 1992.

Surbone, A. et al., "Treatment of the Acquired Immunodeficiency Syndrome (AIDS)and AIDS-Related Complex with a Regimen of 3'-Azido-2'3'-Dideoxythymidine (Aziodthymidine or Zidovudine) and Acyclovir", *Annals of Internal Medicine*, 108: 534-540, 1988.

Surles, J. R. et al, "Multigram Synthesis of 1-Alkylamido Phospholipids," *Lipids*, 28, 55-57, 1993.

Swayze, E. E., et al., "Synthesis of 1-(2-Aminopropyl) Benzimidazoles, Structurally Related to the Tibo Derivative R82150, With Activity Against Human Immunodeficiency Virus," *Bioorganic & Medical Chemistry Letters*, vol. 3, No. 4, pp. 543-546, 1993.

Tarnowski, G. S. et al., "Effect of Lysolecithin and Analogs on Mouse Ascites Tumors", *Cancer Research*, vol. 38, 339-344, 1978.

Tiollais, P., et al., "Hepatitis B. Virus," *Scientific American*, 116-123, Apr. 1991.

van Wijk, G. M. T. et al., "Synthesis and Antiviral Activity of 3'-azido-3'deoxythymidine *Triphosphate distearoylglycerol*: A Novel Phospholipid Conjugate of the Anti-HIV Agent AZT," *Chemistry and Physics of Lipids*, 70, 213-222, 1994.

van Wijk, G. M. T. et al., "Spontaneous and Protein-Mediated Intermembrance Transfer of the *Antiretroviral liponucleotide* 3'-Deoxythymidine Diphosphate Diglyceride," *Biochemistry*, 31, 5912-5917, Jun. 30, 1992.

Yamaue, H. et al., "Chemosensitivity Testing with Highly Purified Fresh Human Tumor Cells with the MTT Colorimetric Assay," *Abstract, Eur J Cancer*, 27:1258-1263, 1991.

Yanagawa, H. et al."Spontaneous Formation of Superhelical Strands," *Journal of the American Chemical Society*, 111, 4567-70, Jun. 21, 1989.

Yarchoan, R. et al., "Therapeutic Strategies in the Treatment of AIDS," *Annual Reports in Medicinal Chemistry*, vol. 23, 253-263, 1988.

LIPID ANALOGS FOR TREATING VIRAL INFECTIONS

CROSS REFERENCE TO RELATED APPLICATIONS

This application is a continuation of U.S. application Ser. No. 09/412,539, filed Oct. 4, 1999, which is a division of U.S. application Ser. No. 08/793,470, filed May 2, 1997, now U.S. Pat. No. 5,962,437, issued Oct. 5, 1999; which is a 371 of International Application No. PCT/US95/10111, filed Aug. 7, 1995; which is entitled to priority to U.S. application Ser. No. 08/314,901, filed Sep. 29, 1994 and to U.S. application Ser. No. 08/297,416, filed Aug. 29, 1994.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

FIELD OF THE INVENTION

This invention relates generally to the treatment of viral infections, and more specifically to the treatment of viral infections with phospholipids and phospholipid derivatives.

BACKGROUND OF THE INVENTION

A current treatment for combating human immunodeficiency virus type 1 (HIV-1) infections is the administration of the nucleoside analog 3'-azido-3'-deoxythymidine (AZT) to an afflicted subject. See, e.g., U.S. Pat. No. 4,724,232 to Rideout et al. HIV-1 infection treatment methods have also included the administration of ether lipid compounds in an amount effective to inhibit replication of the virus in infected cells, see e.g., Kucera et al., *AIDS Research and Human Retroviruses* 6:491 (1990), and ether lipids conjugated with AZT and other antiviral nucleoside analogs. See PCT Application No. US91/04289 (published 26 Dec. 1991). These compounds appear to act at the plasma membrane to block the endocytic process of HIV-1 into CD4$^+$ cells and the process of virus assembly, cell fusion and pathogenesis. They also can inhibit the activity of protein kinase C. Given the seriousness of HIV-1 infection worldwide, there is an ongoing need for new methods of combating HIV-1 infections.

Another virus of serious concern, hepatitis B virus (HBV), is one of a family of hepadnaviruses that cause acute and chronic liver disease, including liver cancer. HBV, which is found in the body fluids of infected persons, makes three antigenic proteins during multiplication in liver cells: hepatitis B surface antigen (HBsAg), hepatitis B e antigen (HBeAg) and hepatitis B core antigen (HBcAg). These three virus antigenic proteins are important as markers for determining virus infection, as antibodies against the virus infection are made in response to these virus proteins in the blood. An HBV vaccine is available to prevent infection, and hyperimmune gamma globulin is available for temporary prophylaxis against developing HBV infection in persons at risk. Clearly specific antiviral agents are needed for treatment and control of HBV infections in humans.

Based on the foregoing, it is an object of the present invention to provide a new treatment method for combating the effects of HIV-1.

It is another object of the present invention to provide compounds and pharmaceutical compositions for carrying out HIV-1 treatment methods.

It is also an object of the present invention to provide a new treatment method for combating the effects of HBV.

It is a second object of the present invention to provide compounds and pharmaceutical compositions for carrying out HBV treatment methods.

SUMMARY OF THE INVENTION

These and other objects are satisfied by the present invention, which provides methods of combating viral infections. As a first aspect, the present invention provides a method of combating a viral infection in a subject in need of such treatment comprising administering to the subject an effective infection-combating amount of a compound of Formula I or a pharmaceutical salt thereof.

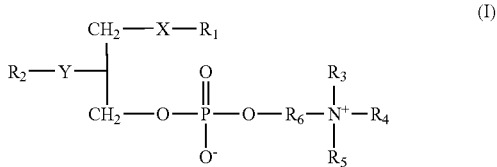

(I)

In the compounds of Formula I, $R_1$ is a branched or unbranched, saturated or unsaturated $C_6$ to $C_{18}$ alkyl group optionally substituted from 1 to 5 times with —OH, —COOH, oxo, amine, or substituted or unsubstituted aromatic; X is selected from the group consisting of NHCO, CH$_3$NCO, CONH, CONCH$_3$, S, SO, SO$_2$, O, NH, and NCH$_3$; $R_2$ is a branched or unbranched, saturated or unsaturated $C_6$ to $C_{14}$ alkyl group optionally substituted from 1 to 5 times with —OH, —COOH, oxo, amine, or substituted or unsubstituted aromatic; Y is selected from the group consisting of NHCO, CH$_3$NCO, CONH, CONCH$_3$, S, SO, SO$_2$, O, NH, and NCH$_3$; $R_6$ is a branched or unbranched $C_2$ to $C_6$ alkyl group; and $R_3$, $R_4$, and $R_5$ are independently methyl or ethyl, or $R_3$ and $R_4$ together form an aliphatic or heterocyclic ring having five or six members and $R_5$ is methyl or ethyl. Preferred compounds include 1-dodecanamido-2-decyloxypropyl-3-phosphocholine, 1-dodecanamido-2-octyloxypropyl-3-phosphocholine, and 1-dodecanamido-2-dodecyloxypropyl-3-phosphocholine. The method is particularly preferred as a treatment to combat viral infections caused by HIV-1, HBV, and herpes simplex virus. The present invention also includes pharmaceutical compositions comprising a compound of Formula I and a suitable pharmaceutical carrier.

As a second aspect, the present invention includes a method of combating viral infections in a subject in need of such treatment which comprises the administration to such a subject a compound of Formula II or a pharmaceutical salt thereof in an effective infection-combating amount.

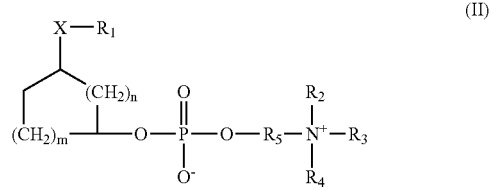

(II)

In Formula II, the ring structure is optionally substituted from 1 to 3 times with $C_1$ to $C_3$ alkyl; $R_1$ is an unbranched or branched, saturated or unsaturated $C_6$ to $C_{20}$ alkyl group; $R_2$, $R_3$, and $R_4$ are independently methyl or ethyl, or $R_2$ and $R_3$ together form an aliphatic or heterocyclic ring having five or six members and $R_4$ is methyl or ethyl; X is selected from the group consisting of NHCO, $CH_3NCO$, CONH, $CONCH_3$, S, SO, $SO_2$, O, NH, and $NCH_3$; $R_5$ is a branched or unbranched $C_2$ to $C_6$ alkyl group; m is 1 to 3; and n is 0 to 2. Preferred compounds of Formula II are 3-hexadecanamido-cyclohexylphosphocholine and 3-hexadecylthio-cyclohexylphosphocholine. Adminstration of the compounds of Formula II is particularly useful in treating viral infections caused by HIV-1, HBV, and herpesviruses. The present invention also includes pharmaceutical compositions comprising a compound of Formula II and a suitable pharmaceutical carrier.

A third aspect of the present invention is a method of treating viral infections comprising administering to a subject in need of such treatment an effective infection inhibiting amount of a compound of Formula III.

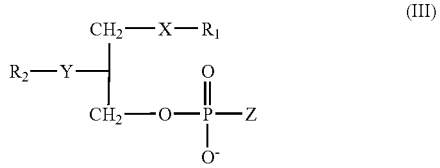
(III)

In compounds of Formula III, $R_1$ is a branched or unbranched, saturated or unsaturated $C_6$ to $C_{18}$ alkyl group optionally substituted from 1 to 5 times with —OH, —COOH, oxo, amine, or substituted or unsubstituted aromatic; X is selected from the group consisting of NHCO, $CH_3NCO$, CONH, $CONCH_3$, S, SO, $SO_2$, O, NH, and $NCH_3$; $R_2$ is a branched or unbranched, saturated or unsaturated $C_6$ to $C_{14}$ alkyl group optionally substituted from 1 to 5 times with —OH, —COOH, oxo, amine, or substituted or unsubstituted aromatic; Y is selected from the group consisting of NHCO, $CH_3NCO$, CONH, $CONCH_3$, S, SO, $SO_2$, O, NH, and $NCH_3$; and Z is a moiety of the Formula V,

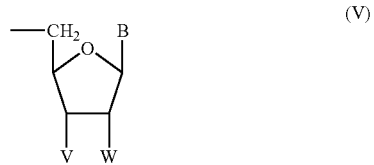
(V)

wherein: V is H or $N_3$;
W is H or F; or
V and W together are a covalent bond; and
B is a purinyl moiety of Formula VI

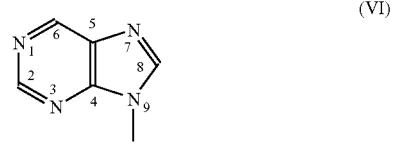
(VI)

optionally substituted at position 2 with =O—OH, —SH, —$NH_2$, or halogen, at position 4 with $NH_2$ or =O, at position 6 with Cl, —$NH_2$, —OH, or $C_1$–$C_3$ alkyl, and at position 8 with Br or I; or B is a pyrimidinyl moiety of Formula VII

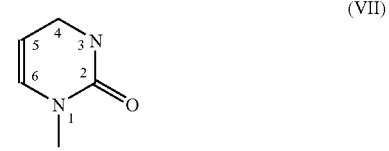
(VII)

substitued at position 4 with =O or $NH_2$ and optionally substituted at position 5 with halogen or $C_1$–$C_3$ saturated or unsaturated alkyl optionally substituted 1 to 3 times with halogen.

Pharmaceutical compositions comprising these compounds and a pharmaceutical carrier are also encompassed by the present invention.

A fourth aspect of the invention is a method of inhibiting viral infections comprising administering to a subject in need of such treatment an effective infection-inhibiting amount of a compound of Formula IV.

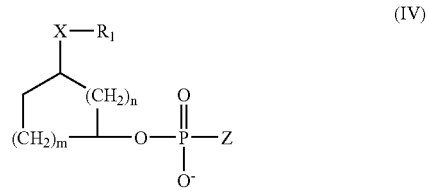
(IV)

In the compounds of Formula IV, the ring structure is optionally substituted from 1 to 3 times with $C_1$ to $C_3$ alkyl; $R_1$ is an unbranched or branched, saturated or unsaturated $C_6$ to $C_{20}$ alkyl group; X is selected from the group consisting of NHCO, $CH_3NCO$, CONH, $CONCH_3$, S, SO, $SO_2$, O, NH, and $NCH_3$; m is 1 to 3; n is 0 to 2; and Z is a moiety of the Formula V,

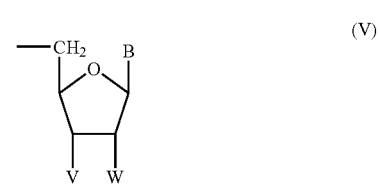
(V)

wherein: V is H or $N_3$;
W is H or F; or
V and W together are a covalent bond; and
B is a purinyl moiety of Formula VI

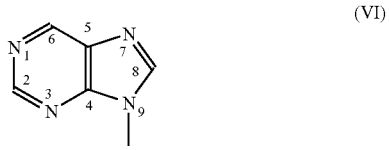
(VI)

optionally substituted at position 2 with =O—OH, —SH, —$NH_2$, or halogen, at position 4 with $NH_2$ or =O, at position 6 with Cl, —$NH_2$, —OH, or $C_1$–$C_3$ alkyl, and at position 8 with Br or I; or B is a pyrimidinyl moiety of Formula VII

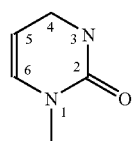

(VII)

substitued at position 4 with =O or $NH_2$ and optionally substituted at position 5 with halogen or $C_1$–$C_3$ saturated or unsaturated alkyl optionally substituted 1 to 3 times with halogen.

The present invention also includes pharmaceutical compositions comprising a compound of Formula IV and a suitable pharmaceutical carrier.

DETAILED DESCRIPTION OF THE INVENTION

As used herein, the term "alkyl" is intended to refer to an unbranched or branched alkyl group comprising carbon atoms, such as methyl, ethyl, propyl, isopropyl, n-butyl, tert-butyl, hexyl, and octyl. The term "pharmaceutical salt" refers to a salt that retains the desired biological activity of the parent compound and does not impart undesired toxicological effects thereto. Examples of such salts are (a) salts formed with cations such as sodium, potassium, $NH_4^+$, magnesium, calcium polyamines, such as spermine, and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

A first aspect of the present invention is a method of combating viral infection comprising administering a compound of Formula I, wherein $R_1$, $R_2$, $R_3$, $R_4$, $R_5$, $R_6$, X, and Y are defined as stated above, or a pharmaceutical salt thereof. The amphipathic compounds of Formula I, which are generally analogs of phosphatidylcholine, include a glycerol backbone (represented by the chain of three carbon atoms to which other functional groups are bonded), lipophilic moieties (represented by $R_1$ and $R_2$) bonded to positions 1 and 2 of the glycerol backbone through functional groups (represented by X and Y) that are generally resistant to phospholipase degradation, and polar phosphate and quaternary amine groups (linked to one another through a short alkyl group) bonded to position 3 of the glycerol backbone. Each of these components of the compounds of Formula I is described separately below.

In Formula I, as described above, $R_1$ is a lipophilic moiety; the lipophilicity of $R_1$ allows the compounds of Formula I to bind with the cell membrane of a cell infected with a retrovirus to provide an anchor thereto. $R_1$ can be an unbranched or branched, saturated or unsaturated $C_6$ to $C_{18}$ alkyl group. Preferably, $R_1$ is an unbranched saturated or unsaturated $C_8$ to $C_{12}$ alkyl group, and more preferably, $R_1$ is an unbranched saturated $C_{10}$ or $C_{12}$ alkyl group.

In compounds of Formula I, X is a functional group that links the lipophilic moiety $R_1$ and the glycerol backbone of the compound. X is selected from the group consisting of NHCO, $CH_3$NCO, CONH, CONCH$_3$, S, SO, $SO_2$, O, NH, and NCH$_3$; these functional groups are resistant to the hydrolytic activity of cellular lipases, in particular phospholipase A, which is specific for ester linkages at position 1 (as are present in phosphatidyl choline). Preferably, X is S or NHCO, with NHCO being most preferred.

In Formula I, $R_2$ is a lipophilic moiety which, as is true for $R_1$, enables the compounds of Formula I to bind with the cell membrane of an infected cell. $R_2$ can be an unbranched or branched, saturated or unsaturated $C_6$ to $C_{14}$ alkyl group. Preferably, $R_2$ is an unbranched saturated or unsaturated $C_8$ to $C_{12}$ alkyl group, and more preferably, $R_2$ is an unbranched saturated $C_8$ or $C_{10}$ alkyl group. It is also preferred that $R_1$ and $R_2$ together contain between 18 and 22 carbon atoms.

$R_2$ is bonded to position 2 of the glycerol backbone through a functional group Y, which is selected from the group consisting of NHCO, $CH_3$NCO, CONH, CONCH$_3$, S, SO, $SO_2$, O, NH, and NCH$_3$. Like X, Y should be a moiety that is resistant to the hydrolytic activity of cellular lipases, and in particular phospholipase B, as this enzyme is specific for ester linkages at position 2. Preferably, X is S or O, with O being more preferred.

The polar hydrophilic end of the amphipathic compounds of Formula I, which can play a role in membrane interaction, comprises an amphoteric phosphoalkyl quaternary amine group in which the phosphate moiety carries the negative charge and the quaternary amine moiety carries the positive charge. In this group, $R_6$, which is a branched or unbranched, saturated or unsaturated $C_2$ to $C_6$ alkyl group, is preferably saturated $C_2$. $R_3$, $R_4$, and $R_5$ are independently selected from the group consisting of methyl and ethyl, with methyl being preferred, and with $R_3$, $R_4$, and $R_5$ each being methyl being more preferred, or $R_3$ and $R_4$ together form an aliphatic or heterocyclic ring having five or six members and $R_5$ is methyl or ethyl.

Exemplary compounds of Formula I include 1-dodecanamido-2-decyloxypropyl-3-phosphocholine (CP-128), 1-dodecanamido-2-octyloxypropyl-3-phosphocholine (CP-130), 1-dodecanamido-2-dodecyloxypropyl-3-phosphocholine (CP-131), and 1-dodecyloxy-2-decyloxypropyl-3-phosphocholine (CP-1 29). These compounds of Formula I can be synthesized according to the procedures set forth in Examples 1 and 2 below. Other compounds of Formula I can be synthesized using the same method with the appropriate reagents substituted for those listed.

Another aspect of the invention is a method of combating viral infection by administering compounds of Formula II, wherein $R_1$, $R_2$, $R_3$, $R_4$, $R_5$, X, m, and n are defined as stated above, or a pharmaceutical salt thereof. Compounds of Formula II are amphipathic moieties having a lipophilic moiety (represented by $R_1$) linked to a five- or six-membered ring structure (which is optionally sustituted 1 to 3 times with $C_1$ to $C_3$ alkyl) and a hydrophilic moiety that includes phosphate and quaternary amine groups linked by a short alkyl group that is bonded to the ring structure through the phosphate group. The hydrophilic group is linked to the ring at position 1, and the lipophilic group is linked to the ring at positions 2, 3, or 4. Like the compounds of Formula I, the compounds of Formula II are analogs of phosphatidyl choline. However, the ring structure provides a more conformationally restricted framework for the compound than compounds lacking a ring structure; this restricted framework can provide the compound with more favorable interaction with the cellular membrane and thereby increase its efficacy.

In the compounds of Formula II, $R_1$ can be an unbranched or branched, saturated or unsaturated $C_6$ to $C_{20}$ alkyl group. As with the compounds of Formulas II, $R_1$ is a lipophilic moiety which binds with the cell membrane of infected cells to provide an anchor thereto. Preferably, $R_1$ is unbranched saturated or unsaturated $C_{10}$ to $C_{18}$ alkyl. More preferably, $R_1$ is unbranched saturated or unsaturated $C_{16}$ to $C_{18}$ alkyl.

In compounds of Formula II, X is a functional group that links the lipophilic moiety $R_1$ to position 1 of the ring structure. X should be a functional group, such as NHCO, $CH_3NCO$, CONH, $CONCH_3$, NH, $NCH_3$, S, SO, $SO_2$, or O, that is able to withstand the hydrolytic activity of cellular lipases. Preferably, Y is S or NHCO.

As stated above, the polar hydrophilic end of the amphipathic compounds of Formula II comprises a phosphate group bonded to the ring structure, a short alkyl group $R_5$ linked at one end thereto, and a quaternary amine group linked to the opposite end of the short alkyl group. $R_5$ is a saturated or unsaturated, branched or unbranched $C_2$ to $C_6$ alkyl group, and is more preferably $C_2$. $R_2$, $R_3$, and $R_4$ are independently selected from the group consisting of methyl and ethyl, with methyl being preferred, or $R_2$ and $R_3$ together form an aliphatic or heterocyclic five- or six-membered ring structure and $R_4$ is methyl or ethyl. It is more preferred that $R_2$, $R_3$, and $R_4$ are each methyl.

In the compounds of Formula II, m can be 1, 2, or 3, and n can be 0, 1, or 2. Preferably the ring structure is a five- or six-membered ring; thus, preferably m is 2 or 3 when n is 0, m is 1 or 2 when n is 1, and m is 1 when n is 2. As noted above, the ring structure provides conformational rigidity to the compound.

Exemplary compounds of Formula II include 3-hexadecylthio-cyclohexylphosphocholine (INK-1), 3-hexadecanamido-cyclohexylphosphocholine, 3-hexadecanamido-cyclopentylphosphocholine, and 3-hexadecylthio-cyclopentylphosphocholine. These compounds of Formula II can be synthesized by following the teachings of Example 3 below in combination with procedures known to those skilled in the art.

An additional aspect of the present invention is a method of combating viral infection with compounds of Formulas III and IV. These compounds substitute a moiety Z for the alkyl-quaternary amine of the compounds of Formulas I and II, wherein Z is as defined above. Z is a moiety that has demonstrated anti-viral activity by itself; thus conjugation of Z to the remainder of the compounds of Formulas III and IV provides a compound that potentially includes multiple active sites for viral inhibition.

In the compounds of Formula III, $R_1$, $R_2$, X and Y are defined above. $R_1$ is a lipophilic moiety; the lipophilicity of $R_1$ allows the compounds of Formula I to bind with the cell membrane of a cell infected with a retrovirus to provide an anchor thereto. $R_1$ can be an unbranched or branched, saturated or unsaturated $C_6$ to $C_{18}$ alkyl group. Preferably, $R_1$ is an unbranched saturated or unsaturated $C_8$ to $C_{12}$ alkyl group, and more preferably, $R_1$ is an unbranched saturated $C_{10}$ or $C_{12}$ alkyl group.

In compounds of Formula III, X is a functional group that links the lipophilic moiety $R_1$ and the glycerol backbone of the compound. X is selected from the group consisting of NHCO, $CH_3NCO$, CONH, $CONCH_3$, S, SO, $SO_2$, O, NH, and $NCH_3$; these functional groups are resistant to the hydrolytic activity of cellular lipases, in particular phospholipase A, which is specific for ester linkages at position 1 (as are present in phosphatidyl choline). Preferably, X is S or NHCO, with NHCO being most preferred.

In Formula III, $R_2$ is a lipophilic moiety which, as is true for $R_1$, enables the compounds of Formula III to bind with the cell membrane of an infected cell. $R_2$ can be an unbranched or branched, saturated or unsaturated $C_6$ to $C_{14}$ alkyl group. Preferably, $R_2$ is an unbranched saturated or unsaturated $C_8$ to $C_{12}$ alkyl group, and more preferably, $R_2$ is an unbranched saturated $C_8$ or $C_{10}$ alkyl group. It is also preferred that $R_1$ and $R_2$ together contain between 18 and 22 carbon atoms.

$R_2$ is bonded to position 2 of the glycerol backbone through a functional group Y, which is selected from the group consisting of NHCO, $CH_3NCO$, CONH, $CONCH_3$, S, SO, $SO_2$, O, NH, and $NCH_3$. Like X, Y should be a moiety that is resistant to the hydrolytic activity of cellular lipases, and in particular phospholipase B, as this enzyme is specific for ester linkages at position 2. Preferably, X is S or O, with O being more preferred.

In the compounds of Formula III, Z is a moiety of Formula V. Moieties of Formula V are intended to be anti-viral agents, and thus potentially provide an additional active site for anti-viral activity that may act through a different mechanism. In the moieties of Formula V, V is H, or $N_3$, or V and W together from a covalent bond with H and $N_3$ being preferred. W is H or F, with H being preferred.

In the compounds of Formula III, B is a purinyl moiety of Formula VI or a pyrimidinyl moiety of Formula VII, each of which are substituted as described above. As used herein, a purinyl moiety comprises six- and five-membered aromatic rings having the molecular structure illustrated in Formula VI. Those skilled in this art will appreciate that the double bonds illustrated in Formula VI are present to represent that the purinyl moieties have aromatic character, and that these double bonds may shift their positions in certain compounds due to the presence of certain substituents to retain the aromatic character of the moiety; in particular, those moieties having =O or $NH_2$ substituents at positions 2 and 4, such as adenine, guanine, xanthine, and hypoxanthine, are generally illustrated as having double bonds shifted from the positions shown in Formula VI. Similarly, as used herein a pyrimidinyl moiety comprises a six-membered aromatic ring having the molecular structure illustrated in Formula VII. Those skilled in this art will appreciate that the double bonds illustrated in Formula VII are included therein to represent that the moieties of Formula VII have aromatic character, and that these double bonds may shift for certain substituents, in particular for =O and $NH_2$ at positions 2 and 4, in order for the moiety to retain its aromatic character. Preferably, B is selected from the group consisting of adenine, thymine, cytosine, guanine, hypoxanthine, uracil, 5-fluorouracil, 2-fluoro-adenine, 2-chloro-adenine, 2-bromo-adenine, and 2-amino-adenine.

Preferably, Z is 3'-azido-3'-deoxythymidine, dideoxyinosine, dideoxycytidine, or 2', 3'-didehydro-3'-deoxythymidine. An exemplary preferred compound of Formula III is 3'-azido-3'-deoxy-5'-(3-dodecanamido-2-decyloxypropyl)-phosphothymidine.

A further aspect of the present invention is a method of inhibiting viral infections comprising administering to a subject an effective infection-inhibiting amount of a compound of Formula IV, wherein $R_1$, $R_2$, X, m, n, and Z are as defined above. In the compounds of Formula IV, $R_1$ can be an unbranched or branched, saturated or unsaturated $C_6$ to $C_{20}$ alkyl group. As with the compounds of Formula II, $R_1$ is a lipophilic moiety which binds with the cell membrane of infected cells to provide an anchor thereto. Preferably, $R_1$ is unbranched saturated or unsaturated $C_{10}$ to $C_{18}$ alkyl. More preferably, $R_1$ is unbranched saturated or unsaturated $C_{16}$ to $C_{18}$ alkyl.

In compounds of Formula IV, X is a functional group that links the lipophilic moiety $R_1$ to position 1 of the ring structure. X should be a functional group, such as NHCO, $CH_3NCO$, CONH, $CONCH_3$, NH, $NCH_3$, S, SO, $SO_2$, or O, that is able to withstand the hydrolytic activity of cellular lipases. Preferably, X is S or NHCO.

As stated above, the polar hydrophilic end of the amphipathic compounds of Formula IV comprises a phosphate group bonded to the ring structure and a moiety Z as defined in Formula V. In the moieties of Formula V, V is H, or $N_3$, or V and W together form a covalent bond, with H and $N_3$ being preferred. W is H or F, with H being preferred.

In the compounds of Formula IV, B is a purinyl moiety of Formula VI or a pyrimidinyl moiety of Formula VII, each of which are substituted as described above. As used herein, a purinyl moiety comprises six- and five-membered aromatic rings having the molecular structure illustrated in Formula VI. Those skilled in this art will appreciate that the double bonds illustrated in Formula VI are present to represent that the purinyl moieties have aromatic character, and that these double bonds may shift their positions in certain compounds due to the presence of certain substituents to retain the aromatic character of the moiety; in particular, those moieties having =O or $NH_2$ substituents at positions 2 and 4, such as adenine, guanine, xanthine, and hypoxanthine, are generally illustrated as having double bonds shifted from the positions shown in Formula VI. Similarly, as used herein a pyrimidinyl moiety comprises a six-membered aromatic ring having the molecular structure illustrated in Formula VII. Those skilled in this art will appreciate that the double bonds illustrated in Formula VII are included therein to represent that the moieties of Formula VII have aromatic character, and that these double bonds may shift for certain substituents, in particular for =O and $NH_2$ at positions 2 and 4, in order for the moiety to retain its aromatic character. Preferably, B is selected from the group consisting of adenine, thymine, cytosine, guanine, hypoxanthine, uracil, 5-fluorouracil, 2-fluoro-adenine, 2-chloro-adenine, 2-bromo-adenine, and 2-amino-adenine.

Preferably, Z is selected from the group consisting of 3'-azido3'-deoxythymidine, dideoxyinosine, dideoxycytidine, and 2', 3'-didehydro-3'-deoxythymidine.

In the compounds of Formula IV, m can be 1, 2, or 3, and n can be 0, 1, or 2. Preferably, the ring structure is a five- or six-membered ring; thus m is 2 or 3 when n is 0, m is 1 or 2 when n is 1, and m is 1 when n is 2. The ring structure provides conformational rigidity to the compound.

An exemplary compound of Formula IV is 3'-azido-3'-deoxy-5'-(3-hexadecylthiocyclohexyl)-phosphothymidine.

Experimentation has demonstrated the efficacy of the compounds of Formulas I, II, III and IV in combating viral infection. For example, compounds CP-128, CP-129, CP-130, CP-131, and INK-1 in nanomolar concentration substantially inhibit the HIV-1 activity in CEM-SS cells. Further, these compounds did so at noncytotoxic levels, thus indicating their promise as therapeutic agents for treatment of viral infections. The compounds of Formulas I, II, III and IV are believed to attach to the cell membrane and thus are particularly effective against infections caused by membrane-containing or envelope-containing viruses, as these viruses typically require access to the cell membrane to multiply and assemble through the manufacture of new viral particles. For example, the compounds of Formulas I, II, III and IV can inhibit the transport and/or incorporation of HIV-1 major glycoprotein gp120 in the cell membrane of an infected cell prior to viral assembly. Such inhibition can block the transmission of infectious HIV-1 into neighboring cells. In addition, compounds of Formulas I, II, III and IV can inhibit the production of the HBV core and "e" antigens, each of which contribute to the assembly of new virus particles and the spread of HBV infection. Other infections for which the compounds of Formulas I, II, III and IV should be efficious include those caused by other membrane-containing or envelope-containing herpesviruses, influenza, respiratory syncytial virus, mumps, measles, and parainfluenza viruses.

Experimentation has also shown that the compounds of Formulae I, II, III, and IV have potent anti-tumor activity. In particular, some of these compounds have $IC_{50}$ values of approximately 1.2 µM against the KB-cell line.

In the manufacture of a medicament according to the invention, hereinafter referred to as a "formulation," the compounds of Formulas I, II, III and IV are typically admixed with, among other things, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5 percent to 95 percent by weight of the active compound. One or more active compounds may be incorporated in the formulations of the invention, which may be prepared by any of the well known techniques of pharmacy consisting essentially of admixing the components.

The formulations of the invention include those suitable for oral, rectal, topical, intrathecal, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or nonaqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like.

Capsules, both hard and soft, are filled with compositions of these active ingredients in combination with suitable diluents and excipients, for example, edible oils, talc, calcium carbonate and the like, and also calcium stearate.

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Liquid preparations for oral administration are prepared in water or aqueous vehicles which advantageously contain suspending agents, for example, methylcellulose, acacia, polyvinylpyrrolidone, polyvinyl alcohol and the like.

Formulations suitable for buccal (sub-lingual) administration include lozenges comprising the active compound in a flavored base, usually sucrose and acacia or tragacanth; and pastilles comprising the compound in an inert base such as gelatin, glycerin, sucrose, or acacia.

Formulations of the present invention suitable for parenteral administration conveniently comprise sterile aqueous preparations of the active compound, which preparations are preferably isotonic with the blood of the intended recipient. These preparations are preferably administered intravenously, although administration may also be effected by means of subcutaneous, intramuscular, intrathecal, or intradermal injection. The formulation should be sufficiently fluid that for easy parental administration. Such preparations may conveniently be prepared by admixing the compound with water or a glycine buffer and rendering the resulting solution sterile and isotonic with the blood. Such preparations should be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Injectable formulations according to the invention generally contain from 0.1 to 5 percent w/v of active compound and are administered at a rate of 0.1 ml/min/kg.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanolin, polyethylene glycols, alcohols, and combinations of two or more thereof. The active compound is generally present at a concentration of from 0.1 to 15 percent w/w, for example, from 0.5 to 2 percent w/w.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, for example, Pharmaceutical Research 3 (6), 318, (1986)) and typically take the form of an optionally buffered aqueous solution of the active compound. Suitable formulations comprise citrate or bis\tris buffer (pH 6) or ethanol/water and contain from 0.1 to 0.2M active ingredient.

The compounds of Formulas I, II, III and IV are administered in an amount sufficient to combat viral infection. The dose can vary depending on the compound selected for administration, the subject, the route of administration, and other factors. Preferably, the compound is administered in an amount of at least 0.1 ng/kg, 1 ng/kg, 0.001 µg/kg or more, and is adminstered in an amount no greater than 0.1 g/kg, 0.01 g/kg, 1 mg/kg, or less.

The invention is illustrated in greater detail in the following nonlimiting examples. In the Examples, "g" means grams, "mg" means milligrams, "µg" means micrograms, "µM" means micromolar, "mL" means milliliters, "° C." means degrees Celsius, "THF" means tetrahydrofuran, "DMF" means dimethylformamide, "mol" means moles, "mmol" means millimoles, and "psi" means pounds per square inch.

EXAMPLE 1

Preparation of Amidoalkyl Derivatives

The procedure set forth below was used to prepare the following compounds:

(a) 1-dodecanamido-2-decyloxypropyl-3-phosphocholine (CP-128)

(b) 1-dodecanamido-2-octyloxypropyl-3-phosphocholine (CP-130)

(c) 1-dodecanamido-2-dodecyloxypropyl-3-phosphocholine (CP-131)

3-Amino-1,2-propanediol was reacted with lauroyl chloride at room temperature in pyridine and dimethyl formamide. The resulting dodecanamido propanediol was recrystallized from chloroform, then reacted with triphenylmethyl chloride. The tritylated product was recrystallized from hexanes. The C-2 hydroxyl was alkylated by reaction with sodium hydride and the appropriate alkyl bromide in tetrahydrofuran for formation of the ether linkage at C-2 (1-bromodecane for CP-128; 1-bromooctane for CP-130; 1-bromododecane for CP-131). Column chromatography on silica gel with a discontinuous gradient of hexanes:ethyl acetate (95:5 to 80:20) produced the desired 1-dodecanamido-2-alkoxy-3-trityloxypropane. Detritylation with p-toluensulfonic acid in 5:1 methylene chloride:methanol gave product having a free primary hydroxyl after column chromatography (hexanes:ethyl acetate 95:5 to 0:100). Reaction with 2-bromoethyl phosphodichloridate in diethyl ether and pyridine produced the phosphate ester, which was purified on silica gel with chloroform:methanol (100:0 to 2:1). Displacement of the bromide with aqueous trimethylamine in chloroform:isopropanol:dimethyl formamide (3:5:5) gave the final phosphocholine product after column chromatography with chloroform:methanol:ammonium hydroxide (70:35:1 to 70:35:7).

EXAMPLE 2

Preparation of
1-dodecyloxy-2-decyloxypropyl-3-phosphocholine
(CP-129)

Isopropylidene glycerol was alkylated using potassium hydroxide and 1-bromododecane in toluene. The resulting ketal was hydrolyzed with hydrochloric acid in methanol, and the diol formed thereby was recrystallized from methanol. The remaining reaction steps (tritylation, alkylation, detritylation, phosphorylation, amination) followed the procedures described above in Example 1 for the alkylamido derivatives.

EXAMPLE 3

Preparation of cis- and trans-3-hexadecylthio-cyclohexylphosphocholine (INK-1)

2-Cyclohexenone (0.14 mol, 13.4 mL) was dissolved in 10 mL of 10 percent sodium hydroxide and 50 mL of THF. An equimolar amount of hexadecyl mercaptan (0.14 mol, 42.9 mL) was added to the unsaturated ketone and the mixture refluxed to produce 3-hexadecylthiocyclohexanone (70 percent yield). This product (5.23 mmol, 1.851 g) was dissolved in methanol and reduced with sodium borohydride (5.23 mmol, 0.199 g) to give a racemic mixture of 3-hexadecylthiocyclohexanol (yield 62 percent; cis:trans ratio 4:1). The phosphorylating agent was prepared by refluxing phosphorus oxychloride (0.65 mol, 60.8 mL) and 2-bromoethanol (0.38 mol, 27.0 mL) in 25 mL of trichloroethylene to produce 2-bromoethyl dichlorophosphate (yield 53 percent). The 3-hexadecylthiocyclohexanol (0.56 mmol, 0.200 g) was dissolved in diethyl ether:THF (2:1) and refluxed with the 2-bromoethyl dichlorophosphate (222 mmol, 0.3 mL) to produce 3-hexadecylthiocyclohexyl phosphoethyl bromide (yield 54 percent). The latter (0.276 mmol, 0.150 g) was dissolved in isopropyl alcohol chloroform:DMF (5:3:5) and heated at 65° C. with trimethylamine (0.042 mol, 2 mL) to produce the desired product, 3-hexadecylthiocyclohexylphosphocholine (yield 38 percent).

This procedure can also be used to prepare 3-alkylthiocyclopentyl derivatives by substituting 2-cyclopentenone.

EXAMPLE 4

Preparation of cis- and trans-3-hexadecanamido-cyclohexylphosphocholine

2-Cyclohexenone is reacted with benzylamine to give 3-benzylaminocyclohexanone. Hydrogenolysis of the benzylamino group then gives 3-aminocyclohexanone. Reaction with hexadecanoyl chloride affords 3-hexadecanamidocyclohexanone, which is then reduced with sodium borohydride to produce a cis/trans mixture of 3-hexadecanamidocyclohexanol. Separation by column chromatography then gives the pure isomers. Reaction with bromoethylphosphodichloridate, then with trimethylamine will produce 3-hexadecanamido-cyclohexylphosphocholine.

Synthesis of the 2- and 4-alkylamido derivatives can be carried out following essentially similar procedures with the substitution of appropriate starting materials.

EXAMPLE 5

Preparation of 3'-azido-3' deoxy-5'-(dodecanamido-2-decyloxypropyl)-phosphothymidine 3-Dodecanamido-2-decyloxy-propanol was synthesized via the scheme described in Morris-Natschke et al., *J. Med. Chem.*, 29:2114 (1986). This alcohol was phosphorylated with diphenylchlorophosphate in pyridine to give the corresponding phosphate ester. The phenyl groups were then removed via hydrolysis with $PtO_2$. The phosphatidic acid derivatives were then conjugated to the 5'-hydroxyl of AZT (DCC condensation).

EXAMPLE 6

Preparation of 3'-azido-3' deoxy-5'-(dodecytoxy-2-decyloxypropyl)-phosphothymidine A. 3-Dodecyloxy-1,2-propanediol[1]

Isopropylidineglycerol (solketal, 26.4 g, 0.20 mol) in 60 mL of toluene was added dropwise to a solution of powdered KOH (22.4 g, 0.04 mol) in 150 mL toluene. The resulting mixture was refluxed for 4 hours. 1-Bromodecane (50 g, 0.20 mol) in 40 mL of toluene was then added dropwise, and the solution was refluxed for 10 hours. After cooling, the reaction mixture was diluted with 200 mL of ice-water and extracted with diethyl ether (3×100 mL). The ether layers were dried over magnesium sulfate, and the solvent was removed in vacuo. The residue was dissolved in 60 mL of diethyl ether and 260 mL of MeOH. Concentrated HCl (60 mL) was added, and the solution was refluxed for 16 hours. After cooling, ice water (150 mL) was added, and the layers were separated. The aqueous layer was extracted with diethyl ether (2×75 mL). The combined organic fractions were then dried over sodium sulfate, filtered, and concentrated in vacuo. The solid residue was recrystallized from MeOH to give 37 g (0.14 mol), 71% of a white solid.

B. 3-Dodecyloxy-1-triphenylmethoxy-2-propanol

The diol synthesized in Section A was tritylated with trityl chloride (59 g, 0.21 mol) in pyridine (200 mL) at 70° C. for 5 hours and then at room temperature overnight. The pyridine was removed under vacuum, and the solid residue was partitioned between water and $CHCl_3$. The $CHCl_3$ layer was washed with 5 percent HCl and water, then dried over magnesium sulfate. After removal of solvent, the product was recrystallized from hexanes:ethyl acetate (10:1) to give 19 g of pure product.

C. 3-Dodecyloxy-2-decyloxy-1-triphenylmethoxypropane

The trityl ether of Section B (13.5 g, 0.027 mol) was added dropwise to an ice-cooled suspension of sodium hydride (80%, 1.6 g, 0.054 mol) in 150 mL of tetrahydrofuran under nitrogen. After stirring for 2 hours at room temperature, heat was applied (55° C.). 1-Bromodecane (6 g, 0.027 mol) was added dropwise; heating was continued for 6 hours. After cooling for 3 hours, water was added slowly. Diethyl ether (2×100 mL) was added, and the solution washed with 15 percent sodium thiosulfite, water, and brine. After drying over sodium sulfate, the ether was removed, and the residue was chromatographed with a gradient of hexanes:ethyl acetate (100:0 to 20:1) to give 9 g (52%) of a clear liquid.

D. 3-Dodecyloxy-2-decyloxy-1-propanol

Detritylation of the product of Section C was accomplished using p-toluenesulfonic acid (0.9 g) in $CHCl_3$: MeOH (72 mL:36 mL) (stirred at room temperature for 48 hours, added 10 percent sodium bicarbonate, extracted with $CHCl_3$, dried over magnesium sulfate, and concentrated). The residue was purified by column chromatography using a gradient of hexanes:ethyl acetate (20:1 to 5:1) to give 3.5 g (63%) of pure 3-dodecyloxy-2-decyloxy-1-propanol.

E. 3-Dodecyloxy-2-decyloxypropyl Diphenyl Phosphate

Diphenylchlorophosphate (0.7 mL, 3.4 mmol) in 10 mL of diethyl ether was cooled to 4° C. under nitrogen. 3-Dodecyloxy-2-decyloxy-1-propanol (1.0 g, 2.6 mmol) in 15 mL of pyridine and 5 mL of diethyl ether was added. The solution was warmed to room temperature then heated to about 52° C. for 3 hours. It was then cooled to room temperature, diluted with 50 mL of diethyl ether, and washed with water (2×25 mL), 0.5 N HCl (25 mL), and then water (25 mL). The organic layer was dried over sodium sulfate, filtered, and concentrated in vacuo to an oil. Chromatography with a gradient of hexanes:ethyl acetate (10:1 to 1:1) produced 980 mg (1.5 mmol, 60%) of pure product.

F. 3-Dodecyloxy-2-decyloxpropyl Phosphate $PtO_2$ (69 mg) was placed in a Parr hydrogenation bottle. The diphenyl phosphate of Section E (500 mg) in 100 mL of EtOH was then added. The reaction mixture was hydrogenated at 15 psi for 1.5 hours until hydrogen uptake ceased. The reaction mixture was then filtered through Celite, and the EtOH was removed in vacuo. The oil was dissolved in 25 mL of pyridine, concentrated in vacuo, and dried under high vacuum to give 350 mg of pure solid phosphatidic acid.

G. 3'-Azido-3'-deoxy-5'-(3-dodecyloxy-2-decyloxypropyl)-phosphothymidine

AZT (43 mg, 0.16 mmol) and the phosphatidic acid of Section F (105 mg, 0.22 mmol) were azeotropically dried with pyridine (3×3 mL) by in vacuo removal. Dicyclohexylcarbodiimide (220 mg, 1.07 mmol) was added, and the drying was repeated 4 times. A final 3 mL portion of pyridine was added, and the reaction mixture was stirred at room temperature in a desiccator for 4 days. Water (1 g) was added, and the mixture was stirred for 4 hours. The solvents were removed in vacuo, and the crude material was chromatographed on 2 g of silica gel using a gradient of $CHCl_3$:MeOH (15:1 to 2:1). The product was dissolved in 11 mL of $CHCl_3$:MeOH:$H_2O$ (4:6:1) and stirred with 1.5 g of Whatman preswollen microgranular cation ($Na^+$) exchange concentrated in vacuo to give 37 mg of product (22%). FAB ms showed a [MH+Na] ion at 752.4350 ($C_{35}H_{64}N_5O_9PNa$, 1.4 ppm) and a $[M+2Na]^+$ ion at 774.4179 ($C_{35}H_{63}N_5O_9PNa_2$, 2.0 ppm).

EXAMPLE 7

Procedure for Assessing Anti-HIV-1 Activity

The inhibitory effects of synthetic phospholipid compounds on the replication of human immunodeficiency virus type 1 (HIV-1) virus in cells was examined by the plaque assay procedure of L. Kucera et al., *Aids Research and Human Retroviruses* 6, 491 (1990). In brief, CEM-SS cell monolayers were infected with HIV-1. Infected cells were overlaid with RPMI-1640 medium plus 10 percent fetal bovine serum (FBS) supplemented with different concentrations of inhibitor. Plaques were counted at five days after infection. In this assay HIV-1 syncytial plaques are seen as large, multicellular foci (10 to 25 nuclei/syncytium) that appear either brown and granular or clear. Since the number of HIV-1 syncytial plaques correlates with reverse transcriptase (RT) and p24 core antigen activity in the HIV-1 infected cell overlay fluids, the syncytial plaque assay can be used to quantify the amount of infectious virus. Reverse transcriptase activity was assayed according to a described procedure (B. J. Poeisz et al., *Proc. Natl. Acad. Scie. (U.S.A.)* 77, 7415 (1980)). The activity of p24 core antigen induced by HIV-1 infection of CEM-SS cells was measured spectrophotometrically using the commercial Coulter EIA.

EXAMPLE 8

Results of Assessment of Anti-HIV-1 Activity

The results (Table 1) showed that all of the lipid compounds tested have an $IC_{50}$ against HIV-1 syncytial plaque formation ranging from 0.11 to 0.64 μM. The compounds' $IC_{50}$ for cell cytotoxicity ranged from 11.85 to 75.7 μM. The highest differential selectivity (611.7), which is a ratio of the cytotoxicity to the anti-HIV-1 activity, was obtained with compound CP-130.

TABLE 1

Evaluation of Ether Lipids for Cytotoxicity and Anti-Viral Activity in CEM-SS Cells IC50 (μM)

| Compounds | Cytotoxicity | Anti-HIV-1 Activity | Differential Selectivity |
|---|---|---|---|
| CP-128 | 31.6 | 0.14 | 225.7 |
| CP-129 | 75.7 | 0.64 | 176.0 |
| CP-130 | 67.2 | 0.11 | 611.7 |
| CP-131 | 36.6 | 0.32 | 114.2 |
| JM-1 (cis) | 11.85 | 0.42 | 28.2 |

Cytotoxicity was measured by uptake of TdR-$H^3$ into total DNA in the presence of serial concentrations of compound.

Anti-HIV-1 activity was measured by standard plaque assay using CEM-SS cell monolayers.

Differential selectivity was determined by dividing the IC50 for cytotoxicity by the IC50 for anti-HIV-1 activity.

EXAMPLE 9

Assessment of HBV Activity Inhibition

Human hepatoblastomas (HepG2) cells were tranfected with plasmid DNA containing tandem copies of HBV genomes. These cells constituitively replicate HBV particles. HepG2 cells were treated with varying concentrations of CP-128 to determine the toxic cell concentration ($TC_{50}$) by neutral red dye uptake. Also, the inhibitory concentration ($IC_{50}$) of CP-128 for HBV replication was determined by ELISA.

It was determined that CP-128 cytotoxicity ($TC_{50}$) was 61.7 μM and the anti-HIV-1 activity ($IC_{50}$) was 15.6 μM (Table 1). These data indicate that CP-128 has selective anti-HBV activity. Mechanism studies indicate that CP-128 can have an inhibitory effect on the cellular production of HBV-induced DNA, core antigen (HBcAg) and "e" antigen (HBeAg). As a result, it is postulated that CP-128 and other compounds of the present invention are likely inhibiting the assembly of HBV nucleocapids and the packaging of viral pregenomic DNA.

The foregoing examples are illustrative of the present invention and are not to be construed as limiting thereof. The invention is defined by the following claims, with equivalents of the claims to be included therein.

What is claimed is:

1. A compound of formula I:

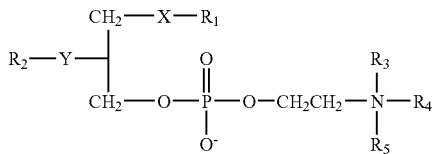

wherein:
- $R_1$ is a branched or unbranched, saturated or unsaturated $C_6$ to $C_{18}$ alkyl group;
- X is selected from the group consisting of —NHC(O)— and —S—;
- $R_2$ is a branched or unbranched, saturated or unsaturated $C_6$ to $C_{14}$ alkyl group;
- Y is selected from the group consisting of —O— and, —S—; and
- $R_3$, $R_4$, and $R_5$ are each independently methyl or ethyl.

2. The compound of claim 1, wherein $R_1$ is an unbranched $C_8$–$C_{12}$ alkyl.

3. The compound of claim 2, wherein $R_1$ is an unbranched $C_{10}$–$C_{12}$ alkyl.

4. The compound of claim 1, wherein $R_2$ is an unbranched $C_8$–$C_{12}$ alkyl.

5. The compound of claim 4, wherein $R_2$ is an unbranched $C_{10}$–$C_{12}$ alkyl.

6. The compound of claim 1, wherein X is —NHC(O) and Y is —O—.

7. The compound of claim 1, wherein X is —NHC(O) and Y is —S—.

8. The compound of claim 1, wherein X is —S and Y is —O—.

9. The compound of claim 1, wherein $R_3$, $R_4$, and $R_5$ are each methyl.

10. The compound of claim 1, wherein
- $R_1$ is a branched or unbranched, saturated or unsaturated $C_6$ to $C_{18}$ alkyl group;
- X is —NHC(O)—;
- $R_2$ is a branched or unbranched, saturated or unsaturated $C_8$ to $C_{12}$ alkyl group;
- Y is —O— and;
- $R_3$, $R_4$, and $R_5$ are each independently methyl or ethyl.

11. The compound of claim 10, wherein $R_3$, $R_4$, and $R_5$ are each methyl.

12. The compound of claim 1, wherein
- $R_1$ is a branched or unbranched, saturated or unsaturated $C_6$ to $C_{18}$ alkyl group;
- X is —NHC(O)—;
- $R_2$ is a branched or unbranched, saturated or unsaturated $C_{10}$ to $C_{12}$ alkyl group;
- Y is —O— and;
- $R_3$, $R_4$, and $R_5$ are each independently methyl or ethyl.

13. The compound of claim 12, wherein $R_3$, $R_4$, and $R_5$ are each methyl.

14. The compound of claim 1, wherein
- $R_1$ is a branched or unbranched, saturated or unsaturated $C_8$ to $C_{12}$ alkyl group;
- X is —NHC(O)—;
- $R_2$ is a branched or unbranched, saturated or unsaturated $C_6$ to $C_{14}$ alkyl group;
- Y is —O— and;
- $R_3$, $R_4$, and $R_5$ are each independently methyl or ethyl.

15. The compound of claim 14, wherein $R_3$, $R_4$, and $R_5$ are each methyl.

16. The compound of claim 1, wherein
- $R_1$ is a branched or unbranched, saturated or unsaturated $C_{10}$ to $C_{12}$ alkyl group;
- X is —NHC(O)—;
- $R_2$ is a branched or unbranched, saturated or unsaturated $C_6$ to $C_{14}$ alkyl group;
- Y is —O— and;
- $R_3$, $R_4$, and $R_5$ are each independently methyl or ethyl.

17. The compound of claim 16, wherein $R_3$, $R_4$, and $R_5$ are each methyl.

18. The compound of claim 1, wherein
- $R_1$ is —$(CH_2)_8$—$CH_3$;
- X is —NHC(O)—;
- $R_2$ is —$(CH_2)_9$—$CH_3$;
- Y is —O—; and
- $R_3$, $R_4$, and $R_5$ are each methyl.

* * * * *